(12) United States Patent
Schulte et al.

(10) Patent No.: US 7,212,289 B1
(45) Date of Patent: May 1, 2007

(54) INTERFEROMETRIC MEASUREMENT DEVICE FOR DETERMINING THE BIREFRINGENCE IN A TRANSPARENT OBJECT

(75) Inventors: Stefan Schulte, Aalen (DE); Uwe Gödecke, Abtsgmünd (DE)

(73) Assignee: Carl Zeiss Smt AG, Oberkochen (DE)

( * ) Notice: Subject to any disclaimer, the term of this patent is extended or adjusted under 35 U.S.C. 154(b) by 422 days.

(21) Appl. No.: 10/299,030

(22) Filed: Nov. 18, 2002

(51) Int. Cl.
*G01B 9/02* (2006.01)

(52) U.S. Cl. .................................. 356/491

(58) Field of Classification Search ............ 356/450, 356/491, 495, 511, 515, 519
See application file for complete search history.

(56) References Cited

U.S. PATENT DOCUMENTS

| | | | | |
|---|---|---|---|---|
| 5,604,591 A | * | 2/1997 | Kitagawa | 356/491 |
| 5,825,492 A | * | 10/1998 | Mason | 356/491 |
| 6,002,480 A | * | 12/1999 | Izatt et al. | 356/479 |
| 6,697,161 B2 | * | 2/2004 | Klein | 356/491 |
| 2002/0024673 A1 | * | 2/2002 | Ouchi | 356/495 |

FOREIGN PATENT DOCUMENTS

WO  WO 03/028073 A1  4/2003

OTHER PUBLICATIONS

M. Totzeck, H. Jacobsen, H.J. Tiziani, "High-resolution measurement of 2D-microstructures by means of Jones-Matrix microscopy", Proceedings der 2$^{nd}$ Conference on Design and Fabrication, Japan 2000.

* cited by examiner

*Primary Examiner*—Gregory J. Toatley, Jr.
*Assistant Examiner*—Michael A. Lyons
(74) *Attorney, Agent, or Firm*—Factor & Lake, Ltd.

(57) ABSTRACT

An interferometric measurement device for determining the birefringence in a transparent object comprises an interferometer with an input for an input light beam. At an output of the interferometer an object light beam passing through the object interferometrically superposes with a reference light beam not passing through the object. A positionally resolving measuring instrument determines at the interferometer output a distribution of phase differences between the object light beam and the reference light beam over the beam cross section of the beams. The measurement device further includes an instrument for modifying the polarization state of the input light beam.

8 Claims, 3 Drawing Sheets

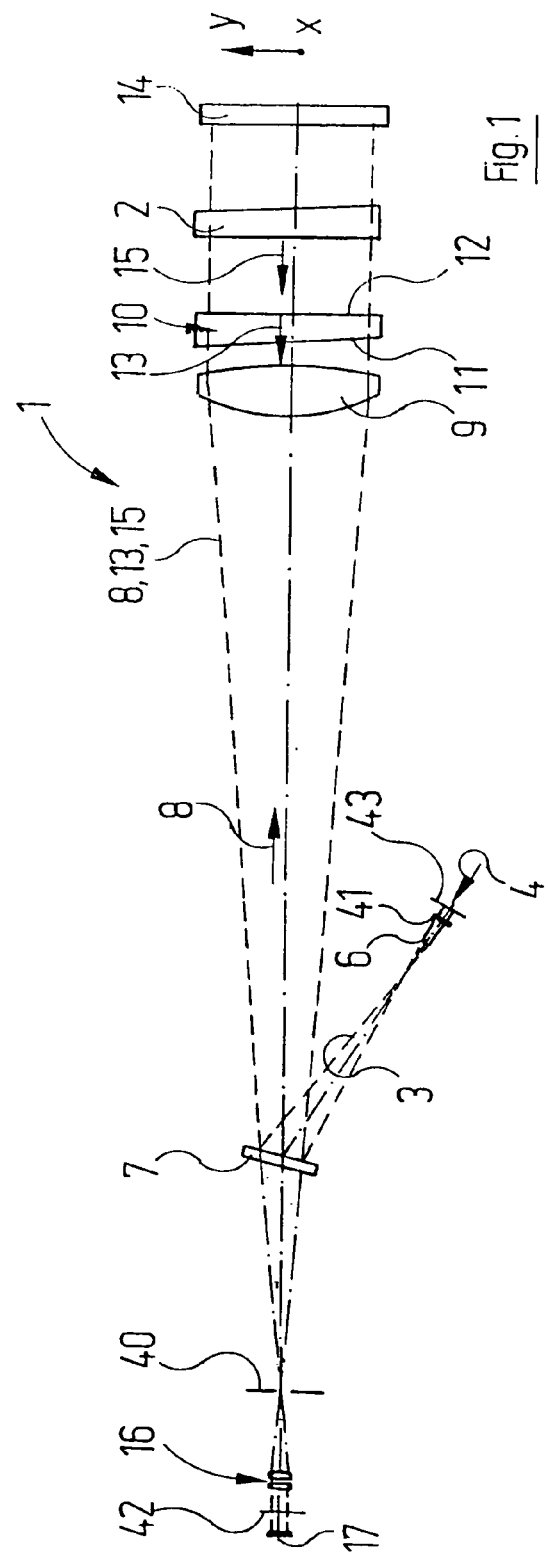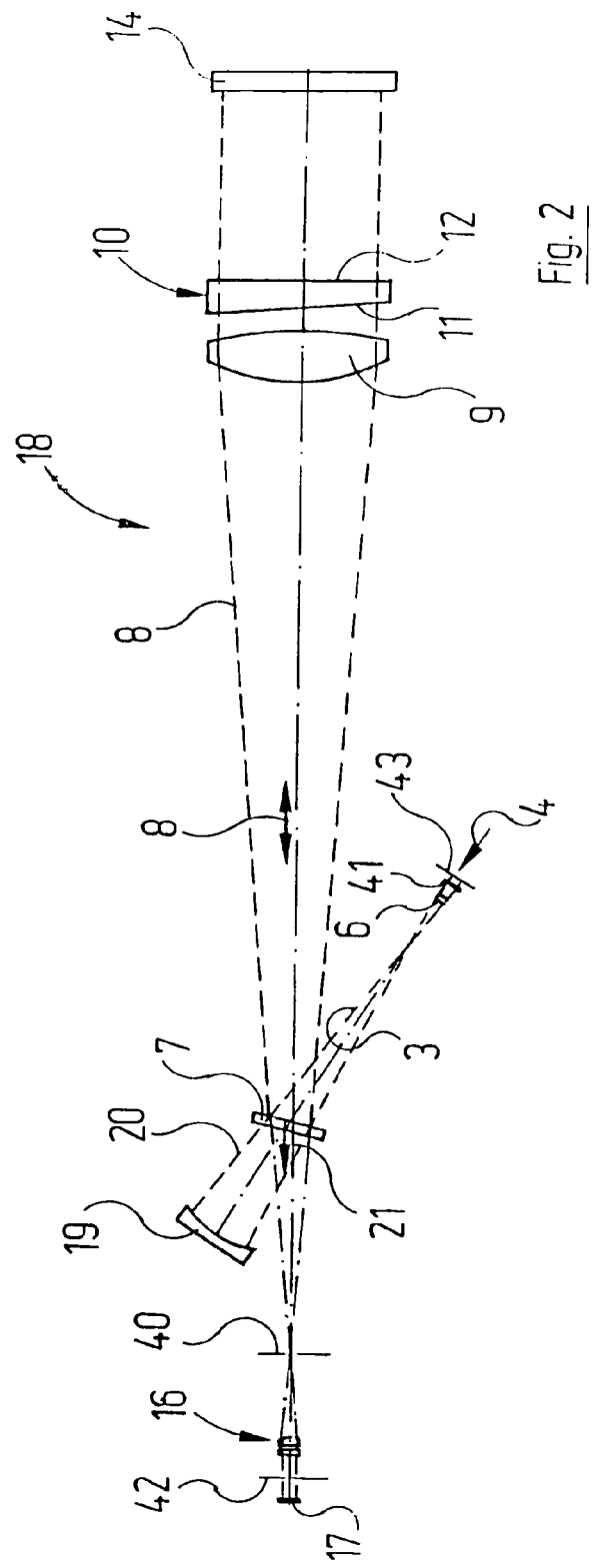

INTERFEROMETRIC MEASUREMENT DEVICE FOR DETERMINING THE BIREFRINGENCE IN A TRANSPARENT OBJECT

FIELD OF THE INVENTION

The invention relates to an interferometric measurement device for determining the birefringence in a transparent object.

DESCRIPTION OF RELATED ART

DE 197 33 890 A1, which corresponds to U.S. Pat. No. 6,172,752 B1, describes a low-coherence interferometric method for birefringence measurement of a transparent object in reflection by means of a Michelson interferometer. The object constitutes the end mirror of one interferometer arm. In order to measure the birefringence, the end mirror of the other interferometer arm is displaced along the optical axis in an oscillatory manner with a fixed frequency for phase modulation. At the same time, either the object or a converging lens focusing the measurement light onto it is displaced in the direction of the optical axis. Depending on the position of the object with respect to the converging lens, the optical path of a measurement beam through the object in the object interferometer arm changes, and this is used for the birefringence measurement.

Owing to the fact that the measurement beam is focused onto the object, only a relatively small section of the object can be analysed with respect to its birefringence in the measurement device according to DE 197 33 890 A1. Another problem with the measurement device according to DE 197 33 890 A1 is that the birefringent effects of the optical components of the measurement device, that is to say not of the object, cannot be separated from the birefringent effects of the object. The measurement accuracy of this known measurement device is therefore limited by the birefringence of the optical components of the measurement device.

In connection with the quality control of optical components for projection objectives in microlithography, the need has arisen to analyse such components, or optical blanks from which such components are made, with respect to their optical properties, as far as possible over their full useful aperture and in a spatially resolved manner. In particular, maximally accurate knowledge of the birefringence of the optical components is necessary. Besides the stress birefringence, this also includes the intrinsic birefringence of optical materials.

A spatially resolved birefringence measurement is not possible, or is only limitedly possible, with the measurement device according to DE 197 33 890 A1, which can provide only integral or, limited by the sections of the object which are acquired by means of the focused measurement beam, section-wise birefringence data of the object.

SUMMARY OF THE INVENTION

It is therefore a first object of the present invention to refine an interferometric measurement device of the type mentioned at the start, in such a way that spatially resolved analysis of the birefringence of the object is possible.

This first object is achieved by an interferometric measurement device for determining the birefringence in a transparent object having a useful aperture, comprising:
an interferometer, which
has an input for an input light beam,
has an output at which an object light beam passing through the object interferometrically superposes with a reference light beam not passing through the object,
a beam-shaping optical arrangement, through which at least the object light beam passes before entry into the object and which is designed in such a way that the object light beam has, when passing through the object, a beam cross section which corresponds to the useful aperture of the object;
a positionally resolving measuring instrument for determining, at the interferometer output, a distribution of phase differences between the object light beam and the reference light beam over the beam cross section of the object light beam and the reference light beam;
an instrument for modifying the polarization state of the input light beam.

According to the invention, is has been found that interferometric superposition of two light beams, one of which does not pass through the transparent object to be analysed with respect to birefringence, is possible with a beam geometry in which positionally resolved determination of the birefringence can be performed in conjunction with further interference patterns, produced with other polarization states of the light entering the measurement device. It is possible to vary the polarization direction of the light beam entering the measurement device and to evaluate the interference patterns produced with the individual polarization directions with respect to their differences, in such a way that the magnitude and the orientation of the birefringence of a specimen is obtained in a spatially resolved manner as a result of this evaluation.

A positionally resolving measuring instrument, in which the positionally resolving measuring instrument is a CCD camera, provides sufficient positional resolution.

With a half-wave plate as the instrument for modifying the polarization state the modification of the polarization state of the light beam entering the interferometer can be carried out in a straightforward way.

If the object and/or a component of the beam-shaping optical arrangement has the shape of a wedge, the creation of additional light beams which might interfere with the measurement is avoided.

If the device comprises at least one further optical component, which produces, in a calibration state of the interferometric measurement device in which the object is removed, a calibration light beam which is guided in such a way that it does not pass through the entire beam-shaping optical arrangement, and which is interferometrically superposed with a light beam that does pass through the entire beam-shaping optical arrangement, the measurement accuracy of the interferometric measurement device according to the invention is improved in such a way that a high absolute measurement accuracy of the birefringence of a specimen is achieved, even in the event of relatively large birefringence contributions from the interferometer components.

As a rule, only relatively few optical components, that is to say essentially the large components such as the collimation lens and a wedge plate, contribute to an equipment-dependent birefringence in the optical setup. For its part, the birefringence of these components is in turn subjected to a measurement in the calibration device. To that end, while in principle maintaining the measurement setup of the interferometric measurement device, a light beam passing through these optical components is superposed with a light beam not passing through them, so that an interference pattern is created. From a plurality of such interference patterns, which have been obtained from different known polarization directions of the light entering the measurement device, it is possible to determine the birefringence of the optical components of the interferometer.

The method for calculating the birefringence from a plurality of interference patterns involves eliminating a polarization-independent but spatially dependent phase offset which, inter alia, is determined by the surface structure of the reference surface and of the specimen, as well as by the homogeneity of the specimen.

BRIEF DESCRIPTION OF THE DRAWINGS

An exemplary embodiment of the invention will be explained in more detail below with reference to the drawing, in which:

FIG. 1 shows an interferometric measurement device for spatially resolved determination of the birefringence of a transparent object;

FIG. 2 shows a calibration device for spatially resolved determination of the birefringence of components of the interferometric measurement device in FIG. 1;

DESCRIPTION OF PREFERRED EMBODIMENTS

Figure 3:
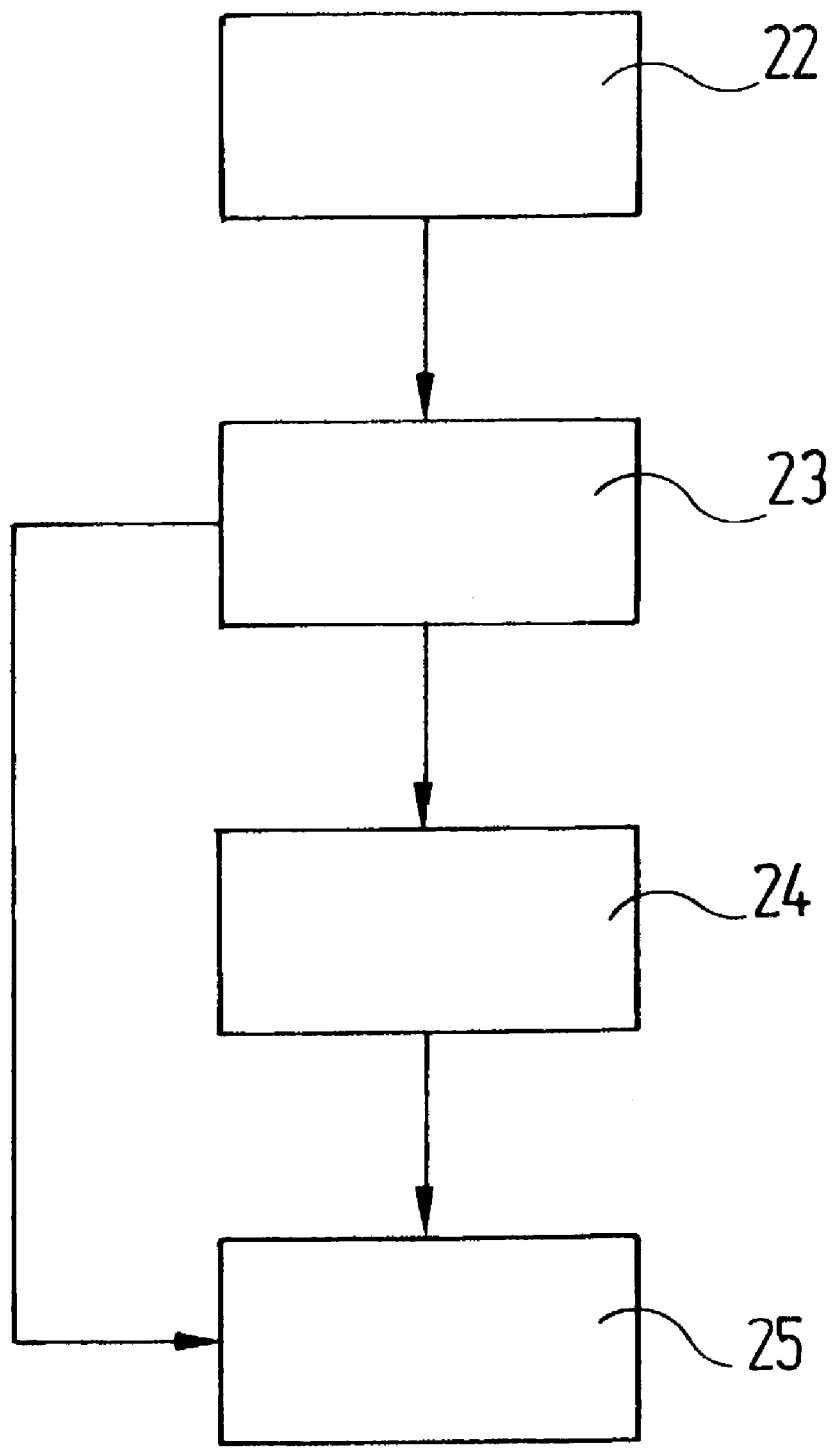
FIG. 3 shows a block diagram of a method for determining the birefringence of an object with the interferometric measurement device in FIG. 1.

An interferometric measurement device 1 for spatially resolved determination of the birefringence, for example the stress birefringence, in a transparent specimen or object 2, for example in an optical blank for a lens of a projection illumination system for microlithography, is shown in FIG. 1 in a meridional section. A measurement light beam 3 is produced by a light source (not shown in the drawing), for example a helium-neon laser with a wavelength of 632.8 nm, and enters the interferometric measurement device 1 in the direction of the arrow 4 through a polarizer 43, which linearly polarizes the beam, and through through a half-wave plate 41. The half-wave plate 41 is mounted rotatably about an axis coinciding with the principal beam direction of the measurement light beam 3.

After passing through the half-wave plate 41, the measurement light beam 3 firstly passes through a lens 6 with positive refractive power for beam shaping. The measurement light beam 3 is in this case firstly focused, and is firstly divergent further along the beam path behind the associated focal plane. It strikes a beam splitter 7 in such a manner.

The measurement light beam 8 which is reflected by the beam splitter 7, and whose principal beam direction after reflection at the beam splitter 7 is again illustrated in FIG. 1 for clarity, passes through a collimation lens 9, which parallelises the reflected measurement light beam 8. After travelling through the collimation lens 9, the measurement light beam 8 strikes a wedge plate 10. The part of the measurement light beam 8 reflected at the entry face 11 of the wedge plate 10 is reflected, because of the wedge shape of the wedge plate 10, out of the measurement beam path of the interferometric measurement device 1 in such a way that it is subsequently no longer relevant and does not interfere with the measurement. This component reflected at the entry face 11, like other reflection beams (not described below) at other faces, is not represented in FIG. 1.

At the face 12 of the wedge plate 10 which is on the rear side in relation to the propagation direction of the measurement light beam 8, a part of the measurement light beam 8 is reflected at a small setpoint tilt angle which is necessary for the interferogram evaluation, and it therefore forms a double-reflected reference light beam 13, the shape of which is identical to the shape of the reflected measurement light beam 8, albeit propagating in the opposite direction and, in contrast to it, at a small setpoint tilt angle.

That component of the measurement light beam 8 which emerges from the wedge plate 10 crosses the full useful aperture of a specimen 2, and is reflected back on itself at an autocollimation mirror 14. After returning through the specimen 2, this component of the measurement light beam 8 reflected back by the autocollimation mirror 14 forms an object light beam 15, which returns back on itself as exactly as possible.

Those components of the reference light beam 13 and of the object light beam 15 which pass through the beam splitter 7 pass through a shutter 40 and an eyepiece 16 consisting of two lenses, as well as a polarizer 42 which rotates synchronously with the half-wave plate 41 but at twice its speed, and which is used as an analyser. The interference pattern resulting from the interferometric superposition of the reference light beam 13 with the object light beam 15 is recorded in a spatially resolved manner by a CCD camera 17.

FIG. 2 shows a calibration device 18 for the interferometric measurement device 1. Components which correspond to those which have already been described with reference to the interferometric measurement device 1 will not be explained again in detail.

The calibration device 18 is derived from the interferometric measurement device 1 by, on the one hand, removing the specimen 2 from the beam path of the interferometric measurement device 1 and, on the other hand, introducing a concave spherical calibration mirror 19 into the beam path of a measurement light beam 20 passing through the beam splitter 7 in the direction of the arrow 4, in such a way that this beam is reflected back on itself. After the reflection at the calibration mirror 19 and a further reflection at the beam-splitter face of the beam splitter 7 in the direction of the eyepiece 16, the measurement light beam 20 forms a reference light beam 21 for the calibration measurement, in which the specimen is constituted by the large interferometer opponents, namely the wedge plate 10 and the collimation lens 9.

The measurement light beam 8 reflected by the beam splitter 7 in the direction of the collimation lens 9 passes through the collimation lens 9 in a similar way to the one described with reference to FIG. 1. There are now two options for the beam path of the measurement light beam 8 which are viable for a calibration measurement:

In the first option, the wedge plate 10 is at the same setpoint tilt angle during the calibration measurement as during a homogeneity measurement or the birefringence measurement of a specimen. The setpoint tilt element is needed in order to produce a multi-fringe interferogram. A part of the measurement light beam 8 is now reflected at the said small setpoint tilt angle at the reference face 12, passes through the wedge plate 10, the collimation lens 9 as well as the beam splitter 7, the shutter 40 and the eyepiece 16, and is superposed with the said reference light beam 20 on the CCD chip of the camera 17 to form a multi-fringe interferogram.

In this case, the autocollimation mirror 14 needs to be tilted in such away that the part of the measurement light beam reflected at its surface cannot reach the camera 17, or cannot pass through the shutter 40 located at the intermediate focus of the camera 17.

In the second option for the calibration measurement, the wedge plate 10 is tilted in such a way that the reflection of the light beam 8 by the wedge plate 10 does not reach the camera 17, but instead the tilt of the autocollimation mirror 14 is adjusted in such a way that the component of the light beam 8 reflected by it is superposed with the light beam 20 on the camera 17 to form a multi-fringe interferogram.

A calibration measurement can be carried out with both described options, since the effect of the birefringence on the wavefront is the same for both possible paths of the light beam 8. Nevertheless, the former option is preferable since the reflection face can in this case keep its standard setpoint tilt and, furthermore, the air path between the wedge surface 12 and the autocollimation mirror 14 is obviated, which leads to better reproducibility.

The calibration device 18 therefore constitutes a Michelson interferometer, the measurement light beam 8 and the calibration light beam 21 each propagating in one of the two interferometer arms.

Figure 4:
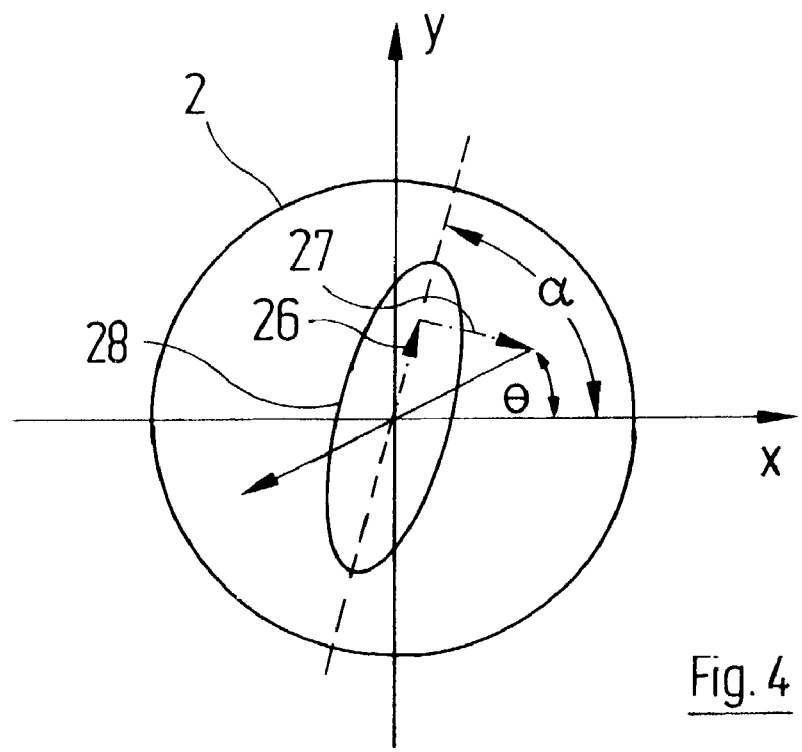
FIG. 4 shows a schematic representation of birefringence ratios in the object.
Figure 5:
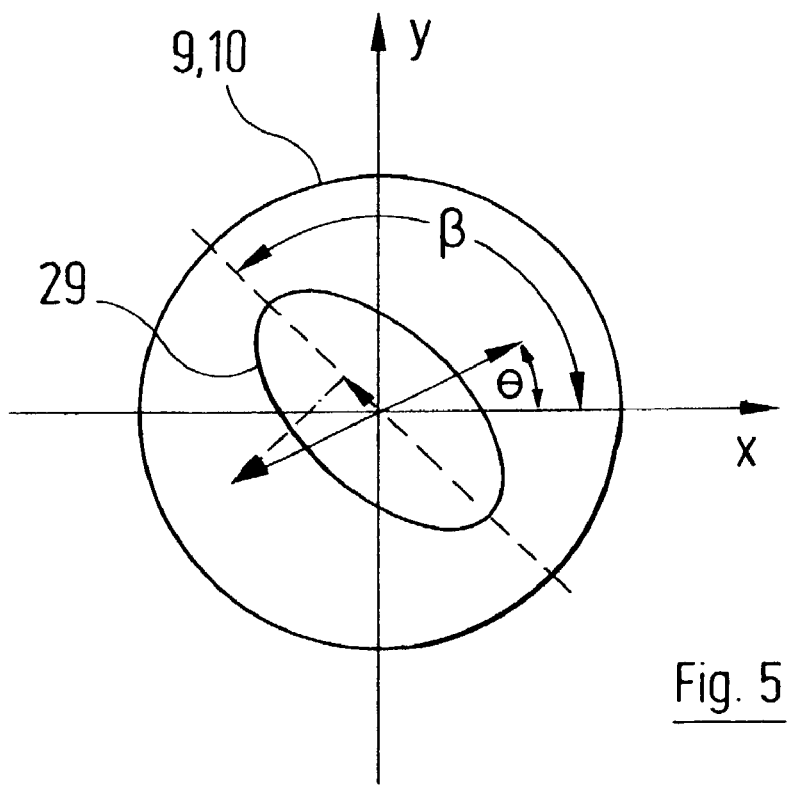
FIG. 5 shows a schematic representation of birefringence ratios in components of the interferometric measurement device.

A method for determining the birefringence, for example the stress birefringence, in the specimen 2 will be described below with reference to FIGS. 3 to 5. FIG. 3 in this case represents a flow chart of the determination method. FIGS. 4 and 5, whose drawing planes are perpendicular to the beam direction of the measurement light beam 8, show the birefringence ratios of the specimen 2 (FIG. 4) as well as of the collimation lens 9 and of the wedge plate 10, which are combined to form an optical superposition component in FIG. 5 for the sake of clarity. The xy coordinate system of FIGS. 4 and 5 is a spatially fixed coordinate system with respect to the interferometric measurement device 1 (cf. FIG. 1).

During the determination method, the birefringences of the collimation lens 9 and of the wedge plate 10 are firstly measured in a measurement step 22, as will be further described below. In an evaluation step 23, the information obtained in the measurement step 22 is subsequently evaluated in such a way that the birefringences of the collimation lens 9 and of the wedge plate 10 can be acquired in a spatially resolved manner with respect to their absolute magnitude as well as their orientation, that is to say the direction of the principal axes of the associated projection of the dielectric tensor.

If the birefringences of the collimation lens 9 and of the wedge plate 10 are negligible, steps 22 and 23 can generally be omitted, so as to obtain a simplified method for determining the birefringence of the specimen 2. Nevertheless, the measurement steps 22 and 23 need to be carried out at least once in order to confirm that the birefringences of the collimation lens 9 and the wedge plate 10 are sufficiently small. Afterwards, the calibration data no longer need to be taken into account for a specimen measurement.

In the simplified method, the interferometric superposition of the reference light beam 13 with the object light beam 15 on the CCD camera 17 is firstly measured in a measurement step 24.

The analytical evaluation of the data found in the measurement step 24 is carried out in the scope of an evaluation step 25 (the exact definition of the abbreviations used for the various quantities is given in the table appended as an annex):

At a particular position on the CCD camera 17, for example at the crossing point of the optical axis of the interferometric measurement device 1 through the measurement plane of the CCD camera 17, the following relationship is obtained for a measured phase difference $\Phi(\text{Theta})$ for an incident measurement light beam 3 with a polarization direction Theta at the crossing point of the optical axis through the specimen 2 (cf. FIG. 4):

$$\Phi(\text{Theta}) = arc\ \tan[\tan \delta \cos 2(\text{Theta} - \alpha)] \qquad (1)$$

In this case, $\delta$ is the magnitude of the birefringence of the specimen 2 at the corresponding lateral position, that is to say the maximum possible optical path difference between two object light beams with differently oriented linear polarizations during a single pass through the specimen 2. It is directly proportional to the thickness of the specimen 2 and to the difference of the dielectric components 26, 27 acting on the object light beam 15, respectively parallel and perpendicular to the long principal axis of the projection of the dielectric tensor of the specimen 2 at the position of the crossing point of the optical axis through the specimen 2, which is depicted by a dielectric ellipse 28 in FIG. 4. $\alpha$ is the angle between the direction of the larger dielectric component 26 of the dielectric ellipse 28 and the x axis.

The measured phase difference $\Phi(\text{Theta})$ contains, besides a phase component $\Phi_m$ caused by the birefringence of the specimen 2, an offset phase component $\Phi_{\textit{offset}}$ which is independent of the polarization direction of the measurement light beam 3 and which is given by the spatially dependent optical path difference along the beam path of the measurement light beam 3 or 8, respectively (for example deviations of the optical faces from the ideal shape, or deviations in the thickness or homogeneity of the specimen 2):

$$\Phi(\text{Theta}) = \Phi_m(\text{Theta}) - \Phi_{\textit{offset}} \qquad (2)$$

The measurement of the phase difference $\Phi(\text{Theta})$ is now carried out for four independent polarization directions (Theta=0°, 45°, 90°, 135°). These different polarization states are produced by corresponding rotations of the half-wave plate 41. In order to rotate the polarization direction of the measurement light beam 3 through 45°, the half-wave plate 41 needs to be rotated, for example, through 22.5°. From the four equations which are thereby obtained owing to the different angles Theta and which are obtained from (1) in conjunction with (2), besides the offset phase component $\Phi_{\textit{offset}}$, the values $\delta$ and $\alpha$ characterising the birefringence in the specimen 2 can be eliminated.

The following are obtained:

$$\delta = arc\ \tan\ 2\sqrt{\tan^2[\Phi_{0/90} - \Phi_{\textit{offset}}] + \tan^2[\Phi_{45/135} - \Phi_{\textit{offset}}]} \qquad (3)$$

$$\alpha = \frac{1}{2} \cdot \arctan 2 \frac{\tan[\Phi_{45/135} - \Phi_{\textit{offset}}]}{\tan[\Phi_{0/90} - \Phi_{\textit{offset}}]} \qquad (4)$$

These values for $\delta$ and $\alpha$ can be determined for each pixel of the CCD camera 17 on the basis of the phase difference $\Phi(\text{Theta})$ measured there, so that a spatially resolved determination of the stress birefringence of the specimen 2 is carried out with the described method.

If the contributions from the interferometric measurement device 1 to the birefringence are not negligible, the results obtained for the birefringence of the collimation lens 9 and the wedge plate 10 in steps 22, 23 of the determination method need to be taken into account computationally. Furthermore, in this case a rotatable polariser, which is used as an analyser 42, is needed in front of the CCD camera 17 for specimen measurements. In this case, these steps are carried out with the aid of the calibration device 18. The rotation of the polariser 41 and the analyser 42 must be synchronised to the extent that the through direction of the analyser 42 coincides with the polarisation direction of the light beam emerging from the Lambda/2 plate 41 and entering the measurement device, that is to say the analyser 42 must be correspondingly aligned with the Lambda/2 plate 41 and it must rotate synchronously with twice the speed of the polariser 41 during the data acquisition.

For the calibration measurement itself, the rotating analyser 42 in front of the CCD camera 17 is not necessary.

The measured spatially resolved calibration phase shift $\Phi_c$(Theta) can be analytically described in a similar way to the phase difference $\Phi$(Theta). In the case of the calibration device 18, the dielectric tensor of the specimen 2 does not affect the measurement light beam 3 since the specimen 2 has been removed. Instead, during the measurement of the phase difference $\Phi_c$(Theta), influence comes from the dielectric tensor of the interferometer components (collimation lens 9, wedge plate 10, cf. FIG. 5), through which the reflected measurement light beam 8 has passed but the calibration light beam 21 has not. The projection of the dielectric tensor, describing the birefringence of the collimation lens 9 and of the wedge plate 10 as a superposition, at the position of the crossing point of the optical axis through these two interferometer components, is represented in FIG. 5 as a dielectric ellipse 29.

birefringence. In this case, the angle $\alpha$ is replaced by the angle beta between the long principal axis of the dielectric ellipse 29 and the x axis, and the phase lag $\delta$ due to the specimen 2 is replaced by the phase lag gamma caused by a single pass through the collimation lens 9 and the wedge plate 10.

During this calibration measurement as well, measurement is in turn carried out with four different polarizations of the measurement light beam 3, as described above in connection with the analysis of the specimen 2 in the case negligible interferometer errors.

After carrying out and evaluating the calibration measurement in steps 22 and 23, the calibration mirror 19 is removed, or more preferably shielded by a shutter, and the specimen 2 is put into the interferometric measurement device 1. The phase difference $\Phi$(Theta) then spatially resolved by the CCD camera 17 in the case of non-negligible birefringences of the large interferometer components (collimation lens 9 and wedge plate 10), which results from the superposition of that due to the stress birefringence of the specimen 2, on the one hand, as well as of the collimation lens 9 and of the wedge plate 10, on the other hand, can be analytically written as:

$$\Phi_{sample}(\theta) = \Phi_{meas} - \Phi_{offset} =$$

$$\arctan2 \frac{\sin\gamma \cdot \cos2(\theta - \beta) + \frac{1}{2}\tan\delta\{(1+\cos\gamma) \cdot \cos2(\theta - \beta) - (1-\cos\gamma) \cdot \cos2(\theta + \alpha - 2\beta)\}}{(\cos\gamma - \cos2(\alpha - \beta) \cdot \sin\gamma \cdot \tan\delta)} -$$

$$\arctan2[\tan\gamma \cdot \cos2(\theta - \beta)]$$

If gamma tends to 0, that is to say for negligible interferometer contributions to the birefringence, formula (1) is obtained from this.

This measurement is in turn carried out with four different polarization directions of the measurement light beam 3. From the analytical descriptions assigned to these four measurement polarizations, it is in turn possible to eliminate the values $\alpha$, $\delta$ characterising the stress birefringence of the specimen 2. The following are obtained:

$$\alpha = \frac{1}{2}\arctan2 \frac{A_{0/90} \cdot \sin2\beta - B_{45/135} \cdot \cos2\beta}{\sin\gamma - \cos\gamma \cdot [A_{0/90}\cos2\beta + B_{45/135}\sin2\beta]} - \beta \text{ with} \quad \text{(Formulae 6 and 7)}$$

$$A_{0/90} = \frac{\tan\gamma \cdot \cos2\beta \pm \tan(\Phi_{0/90} - \Phi_{offset})}{1 \mp \tan\gamma \cdot \cos2\beta \cdot \tan(\Phi_{0/90} - \Phi_{offset})}$$

$$B_{45/135} = \frac{\tan\gamma \cdot \sin2\beta \pm \tan(\Phi_{45/135} - \Phi_{offset})}{1 \mp \tan\gamma \cdot \sin2\beta \cdot \tan(\Phi_{45/135} - \Phi_{offset})}$$

$$\delta = \arctan2 \frac{B_{45/135} \cdot \cos\gamma - \sin\gamma \cdot \sin2\beta}{\cos2(\alpha - \beta) \cdot [B_{45/135} \cdot \sin\gamma + \sin2\beta \cdot \cos\gamma] + \sin2(\alpha - \beta) \cdot \cos2\beta}$$

The description given above in connection with the measurement of the birefringence of the specimen 2 in the case of negligible interferometer errors can be applied fully to the calibration measurement of the stress birefringence of the collimation lens 9 and of the wedge plate 10, since it can be assumed that the small interferometer components, such as the beam splitter 7 and eyepiece 16, do not have any Therefore, even in event of non-negligible stress birefringence contributions from the collimation lens 9 and the wedge plate 10, a spatially resolved analysis of the stress birefringence of the specimen 2 is possible.

With the described method, a spatially resolved analysis of the stress birefringence of the specimen 2 can be carried out in the 0.1 nm/cm range. The spatial resolution is in this case limited only by the spatial resolution of the detector, in this case the CCD camera 17.

| Physical quantity | Meaning |
|---|---|
| $\delta$ | spatially dependent stress birefringence of the specimen (phase lag between the slow and fast principal axes in a single pass). This is the most important quantity to be determined |
| $\alpha$ | spatially dependent angle between the x axis of the interferometer coordinate system and the fast principal axis of the specimen. This quantity is jointly determined in the scope of the SBR calculation. |
| Theta | Angle between the x axis of the interferometer coordinate system and the direction of the electric field vector of the radiation entering the measurement device |
| $\Phi$ (Theta) | The spatially dependent phase measured by the interferometer as a function of Theta |
| $\Phi_m$ (Theta) | The component of $\Phi$ (Theta) which varies with the polarisation direction of the incident radiation, m takes the angle values 0°, 45°, 90° and 135° |
| $\Phi_0$ | The component of $\Phi$ (Theta) which is independent of the polarisation direction of the incident radiation, caused by spatially dependent optical path differences (for example conformity, thickness, homogeneity) |
| $\Phi_c$ (Theta) | Phase profile measured during the SBR calibration, similar to $\Phi$ (Theta) |
| $\gamma$ | spatially dependent birefringence of the interferometer components, (similar to $\delta$). This quantity is determined during the SBR calibration of the interferometer. |
| $\beta$ | spatially dependent angle between the x axis of the interferometer coordinate system and the fast principal axis of the interferometer optics (similar to $\alpha$). This quantity is determined in the scope of the SBR interferometer calibrations. |

The invention claimed is:

1. An interferometric measurement device for determining the birefringence in a transparent object having a useful aperture, comprising:
    an interferometer, which
        has an input for an input light beam,
        has an output at which an object light beam passing through the object interferometrically superposes with a reference light beam not passing through the object,
    a beam-shaping optical arrangement, through which at least the object light beam passes before entry into the object and which is designed in such a way that the object light beam has, when passing through the object, a beam cross section which corresponds to the useful aperture of the object;
    a positionally resolving measuring instrument for determining, at the interferometer output, a distribution of phase differences between the object light beam and the reference light beam over the beam cross section of the object light beam and the reference light beam; an instrument for modifying the polarization state of the input light beam; and,
    at least one further optical component, which produces, in a calibration state of the interferometric measurement device in which the object is removed, a calibration light beam which is guided in such a way that it does not pass through the entire beam-shaping optical arrangement, and which is interferometrically superposed with a light beam that does pass through the entire beam-shaping optical arrangement.

2. The interferometric measurement device of claim 1, wherein the positionally resolving measuring instrument is a CCD camera.

3. The interferometric measurement device of claim 1, wherein the instrument for modifying the polarization state is a half-wave plate.

4. The interferometric measurement device of claim 1, wherein the object has the shape of a wedge.

5. The interferometric measurement device of claim 1, wherein the at least one further optical component comprises:
    a reflecting beam splitter that splits off a part from the input light beam, said part forming the calibration light beam,
    a mirror that reflects the calibration light beam towards the beam splitter from where it is reflected towards the positionally resolving measuring instrument.

6. The interferometric measurement device of claim 1, wherein the beam-shaping optical arrangement comprises at least one optical component has the shape of a wedge.

7. A method of calibrating a measurement device for determining the birefringence in a transparent object having a useful aperture, said device comprising:
    an interferometer, which
        has an input for an input light beam,
        has an output at which an object light beam passing through the object interferometrically superposes with a reference light beam not passing through the object,
    a beam-shaping optical arrangement, through which at least the object light beam passes before entry into the object and which is designed in such a way that the object light beam has, when passing through the object, a beam cross section which corresponds to the useful aperture of the object;
    a positionally resolving measuring instrument for determining, at the interferometer output, a distribution of phase differences between the object light beam and the reference light beam over the beam cross section of the object light beam and the reference light beam;
    an instrument for modifying the polarization state of the input light beam, at least one further optical component, which produces, in a calibration state of the interferometric measurement device in which the object is removed, a calibration light beam which
        is guided in such a way that it does not pass through the entire beam-shaping optical arrangement, and which
        is interferometrically superposed with a measurement light beam that does pass through the entire beam-shaping optical arrangement,
    wherein the method comprises the following steps:
    a) measuring phase differences between the calibration light beam and the measurement light beam with different polarization settings;
    b) determining the birefringence of optical components of the beam-shaping optical arrangement through which the measurement light beam passes, but through which the calibration light beam does not pass, over the beam cross section by analyzing the phase differences measured in step a); and
    c) storing the determined birefringence in a memory device.

8. The method of claim 7, comprising the step of eliminating an offset component which is due to polarization-independent and spatially dependent optical path differences in the measurement device being in the calibration state.

* * * * *